US009285317B2

(12) United States Patent
Thabeth et al.

(10) Patent No.: US 9,285,317 B2
(45) Date of Patent: Mar. 15, 2016

(54) APPARATUS AND METHOD FOR DETERMINING THE AMOUNTS OF TWO OR MORE SUBSTANCES PRESENT IN A LIQUID

(71) Applicant: ADVANCED SENSORS LIMITED, Carrickfergus, County Antrim (GB)

(72) Inventors: Khalid Thabeth, County Antrim (GB); Stephen Taylor, Liverpool (GB)

(73) Assignee: Advanced Sensors Limited, Carrickfergus, County Antrim (GB)

( * ) Notice: Subject to any disclaimer, the term of this patent is extended or adjusted under 35 U.S.C. 154(b) by 36 days.

(21) Appl. No.: 14/272,645

(22) PCT Filed: Nov. 5, 2012

(86) PCT No.: PCT/EP2012/071861
§ 371 (c)(1),
(2) Date: May 8, 2014

(87) PCT Pub. No.: WO2013/068320
PCT Pub. Date: May 16, 2013

(65) Prior Publication Data
US 2015/0285740 A1    Oct. 8, 2015

(30) Foreign Application Priority Data
Nov. 9, 2011   (GB) .................................. 1119352.1

(51) Int. Cl.
*G01J 1/58*       (2006.01)
*G01N 21/00*      (2006.01)
*G01N 21/64*      (2006.01)
*H01J 49/26*      (2006.01)
*H01J 49/00*      (2006.01)

(52) U.S. Cl.
CPC .......... *G01N 21/645* (2013.01); *H01J 49/0009* (2013.01); *H01J 49/0027* (2013.01); *H01J 49/26* (2013.01); *G01N 2201/06113* (2013.01)

(58) Field of Classification Search
USPC ............. 250/301, 458.1, 459.1, 461.1, 462.1, 250/483.1, 484.2, 484.4, 486.1; 73/61.48, 73/53.01; 356/928
See application file for complete search history.

(56) References Cited

U.S. PATENT DOCUMENTS

| | | | |
|---|---|---|---|
| 5,381,002 A * | 1/1995 | Morrow et al. ................ | 250/301 |
| 7,460,981 B2 | 12/2008 | Bultman et al. | |
| 7,935,938 B2 * | 5/2011 | Thabeth et al. ............ | 250/458.1 |
| 2005/0088646 A1 * | 4/2005 | Kong et al. ..................... | 356/70 |
| 2009/0032733 A1 * | 2/2009 | Thabeth et al. ............ | 250/458.1 |
| 2011/0224516 A1 | 9/2011 | Romey et al. | |

FOREIGN PATENT DOCUMENTS

| | | |
|---|---|---|
| EP | 0259951 A2 | 3/1988 |
| WO | 2007096179 A1 | 8/2007 |

* cited by examiner

*Primary Examiner* — Bernard E Souw
(74) *Attorney, Agent, or Firm* — Gunn, Lee & Cave, P.C.

(57) ABSTRACT

An apparatus for determining the total amount of two or more substances in a liquid, at least one of said substances comprising a fluorescent substance, said apparatus comprising: a mass spectrometer device; a fluorometer device; and a processing means; wherein said mass spectrometer device is adapted to obtain a periodic measurement of the total amount of said two or more substances in the liquid, said fluorometer device being adapted to detect the fluorescent response of said at least one fluorescent substance in said liquid to an excitation signal, said processing means being programmed to determine a calibration factor by comparing a measurement obtained by the fluorometer device with said periodic measurement of the total amount of said two or more substances present obtained by the mass spectrometer device, the processing means subsequently using said calibration factor to determine measurements representative of the total amount of both fluorescent and non-fluorescent substances present in the liquid based upon the fluorescent response detected by the fluorometer device.

21 Claims, 2 Drawing Sheets

|  | PPM |
|---|---|
| Ethene | 572.40 |
| Ethane | 2.40 |
| Methanol | 346.90 |
| Propene | 0.70 |
| Propane | 77.30 |
| Ethanol | 0.30 |
| Total Hydrocarbons Present | 1000.00 |

Figure 2

| Measurment | Secodary Techniqe Total PPM | Ethene | Ethane | Methanol | Propene | Propane | Ethanol |
|---|---|---|---|---|---|---|---|
| 1 | 1000 | 572.4 | 2.4 | 346.9 | 0.7 | 77.3 | 0.3 |
| 2 | 900 | 515.16 | 2.16 | 312.21 | 0.63 | 69.57 | 0.27 |
| 3 | 800 | 457.92 | 1.92 | 277.52 | 0.56 | 61.84 | 0.24 |
| 4 | 700 | 400.68 | 1.68 | 242.83 | 0.49 | 54.11 | 0.21 |
| 5 | 500 | 286.2 | 1.2 | 173.45 | 0.35 | 38.65 | 0.15 |

Figure 3

APPARATUS AND METHOD FOR DETERMINING THE AMOUNTS OF TWO OR MORE SUBSTANCES PRESENT IN A LIQUID

This invention relates to an apparatus and method for determining the amounts of two or more substances present in a liquid, and in particular, to the identification and measurement of the amount of each of two or more different compounds, including at least one hydrocarbon compound, in a liquid, particularly water.

There are many applications that require the determination of the presence of, and amount of, oil or other substances or additives present in a liquid. For example, in pipes leading from oil production or refining facilities it may be required to identify and measure the amount of oil that is present in the liquid flowing in the pipes.

Many hydrocarbon compounds and other substances have a natural fluorescence. Therefore it is known to measure the amount or concentration of a particular oil or other fluorescent substance in a liquid by the detection of fluorescence. Devices that detect and/or measure fluorescence are commonly referred to as fluorometers. A fluorometer usually includes a light source for causing excitation of a target substance and a detector for measuring the resultant fluorescence of the target substance at a predetermined wavelength. EP 1991856 (incorporated herein by reference) discloses a fluorometer for determining the amount of a fluorescent substance, in a liquid, such as water.

One problem with existing fluorometers is that there can be a vast difference in the amplitude of measured fluorescence between different fluorescent substances at the same concentration. Therefore a known fluorometer calibrated for one type of oil or other fluorescent substance will produce inaccurate results when a different type or oil or substance is present in the liquid. For example, when a fluorometer is calibrated for a QAV medium, a concentration of 650 ppm will be indicated with Salted Petroleum, even though only 10 ppm is actually present, due to the much greater amplitude of fluorescence of Salted Petroleum compared to QAV medium. This becomes an even bigger problem when a mixture of two or more fluorescent substances are present. A second problem is that such known fluorometers are unable to detect the presence of non-fluorescent compounds in such mixture and thus may give a highly inaccurate determination of the total amount of oil, other substances or additives in a liquid, such as water, where the liquid contained a mixture of fluorescent and non-fluorescent substances.

Mass spectrometers can be used to identify each compound present in a mixture and can determine the amount of each compound present (based upon calibration data obtained from sample testing). However, the analysis of a mixture using mass spectroscopy is relatively slow, expensive and difficult to carry out outside of a laboratory environment and is therefore generally unsuitable of real time monitoring of the presence and amounts of contaminants or additives, such as oil, in liquids. By contrast, fluoroscopy is a relatively fast, robust and effective way of measuring the amount of a fluorescent substance present in a liquid in real time, albeit with the abovementioned limitations.

An objective of the present invention is to provide a method and apparatus for determining the amounts of two or more substances present in a liquid that combines the accuracy of mass spectroscopy with the speed and robustness of fluoroscopy.

According to a first aspect of the present invention there is provided an apparatus for determining the total amount of two or more substances in a liquid, such as water, at least one of said substances comprising a fluorescent substance, said apparatus comprising:—
a mass spectrometer device
a fluorometer device, and
a processing means
wherein said mass spectrometer device is adapted to obtain a periodic measurement of the total amount of said two or more substances in the liquid,
said fluorometer device being adapted to detect the fluorescent response of said at least one fluorescent substance in said liquid to an excitation signal,
said processing means being programmed to determine a calibration factor by comparing a measurement obtained by the fluorometer device with said periodic measurement of the total amount of said two or more substances present obtained by the mass spectrometer device, the processing means subsequently using said calibration factor to determine measurements representative of the total amount of both fluorescent and non-fluorescent substances present in the liquid based upon the fluorescent response detected by the fluorometer device.

Said apparatus may be adapted to obtain further periodic measurements of the total amount of said two or more substances in the liquid by periodic operation of said mass spectrometer device to update said calibration factor at selected intervals.

Preferably said mass spectrometer device both identifies each of said two or more substances present and provides a measurement the amount of each of said two or more substances present in the liquid, said processing means subsequently determining the amount of each of said two or more substances present as a function of the measurements obtained by the fluorometer device and the relative proportions of said two or more substances in said liquid determined by the mass spectrometer device.

The data obtained by said mass spectrometer device is thereby subsequently used to deconstruct or interpret the spectral response data obtained by said fluorometer device, due to the fluorescent response of said at least one fluorescent substance present in the liquid, to determine the amount of each of said two or more substances, comprising both fluorescent and non-fluorescent substances, present in said liquid from the data obtained by the fluorometer device. Thus the fluorometer device can be used to determine the amount of a non-fluorescent substance present in the liquid based on the assumption that the relative proportions of each of said two or more substances present in the liquid does not change, or only changes slowly, over a period of time between periodic measurements obtained by said mass spectrometer device.

The periodic data obtained by the mass spectrometer device may be updated by periodic operation of the mass spectrometer device at intervals selected to reflect the expected rate of change of the relative proportions of said two or more substances present in the liquid over time.

Preferably said processing means includes memory means for recording data obtained from the mass spectrometer device to enable said data to be subsequently used to interpret the spectral response date obtained by the fluorometer device. Preferably said memory means is also adapted to record data obtained by the fluorometer device over time.

The mass spectrometer is able to periodically recalibrate the fluorometer device by determining the identity and proportions or and/amounts of said two or more fluorescent substances so that the output of the fluorometer device can provide an accurate determination of the amounts of each substance present.

Preferably the mass spectrometer device comprises a membrane introduction mass spectrometer (MIMS) having a permeable membrane through which said two or more substances present in the liquid, in particular hydrocarbons, can pass to be ionised within the mass spectrometer device. Preferably the mass spectrometer device is provided with an evacuated chamber, said membrane being associated with an entrance port of the evacuated chamber whereby said two or more substances may pass through the membrane to be introduced into the mass spectrometer device.

Preferably the membrane comprises a hydrophobic membrane.

Preferably the apparatus includes an ultrasonic transducer for applying ultrasonic energy to the membrane, preferably via the liquid adjacent the membrane, to keep the membrane clear from dirt and blockages. The ultrasonic transducer may be associated with the fluorometer device such that a viewing window of the fluorometer device is kept clean by means of the ultrasonic transducer. Such arrangement may be as described in WO 2007/096179, incorporated herein by reference. The exposure of the liquid to ultrasonic vibrations may also provide a homogeneous uniformly representative sample for analysis by the apparatus.

The membrane may define a wall portion of a sampling chamber. Alternatively the membrane may be provided at an end of an evacuated tube extending into the sampling chamber. Preferably the membrane is located adjacent a measurement window of the fluorometer device formed in a wall of the sampling chamber.

In one embodiment, said fluorometer device may be associated with a primary sampling chamber for receiving a liquid to be analysed whereby the fluorescent response of said liquid can be determined and analysed, said mass spectrometer device being associated with a secondary sampling chamber arranged in parallel with said primary sampling chamber so that said liquid to be analysed may be periodically diverted to said secondary sampling chamber to enable periodic determination of the identify and relative proportions of said two or more substances by said mass spectrometer such that the data from the mass spectrometer used to interpret the data from the fluorometer device can be periodically updated. One or more valves maybe provided for periodically diverting said liquid to be analysed to the secondary sampling chamber.

According to a further aspect of the present invention there is provided a method for determining the amounts of two or more substances, preferably in the form of organic compounds, in a liquid, such as water, said method comprising the steps of determining the total amount of said two or more substances in said liquid by means of a mass spectrometer device, exposing said liquid to an excitation source for exciting said two or more fluorescent substances, and detecting the fluorescent response of the substances within the liquid, and determining the total amount of said two or more substances present in the liquid based upon the fluorescent response of the substances calibrated as a function of the total amount of substance present determined by the mass spectrometer.

According to a further aspect of the present invention there is provided a method of determining the amounts of two or more compounds in a liquid, such as water, said method comprising using a first technique to determine the total amount of substantially all compounds present in the liquid and using a second technique to determine the amount of at least one of the two or more compounds present in said liquid, the measurement obtained by the second technique being calibrated by the measurement obtained from the first technique, such that the total amount of said two or more compounds present in the liquid can be determined using the data obtained by said second technique over a period of time based upon an assumption that the relative proportions of said two or more compounds present does not change significantly over said period of time.

Preferably said total amount of said two or more compounds present is determined using said first technique after said period of time to thereby recalibrate said second technique.

Preferably said first technique comprises mass spectrometry.

Preferably said second technique comprises fluoroscopy or absorption spectroscopy.

Thus the data obtained by said first technique may be used to deconstruct the data obtained by the second technique, whereby the data obtained by the second technique may be used to determine the amount or concentration of each of said two or more compounds present within said liquid.

Said first technique may be carried out intermittently to periodically recalibrate said second technique. The second technique may be carried out continuously.

Once the total amount of said two or more compounds present in said liquid has been determined by said first technique, data obtained by said second technique, calibrated by the data obtained from the first technique, may be subsequently used to determine the total amount of said two or more compounds present and may also be used to determine the amount of each of each of said two or more compounds present in said liquid based upon the relative proportions of each of said two or more compounds as determined by the first technique.

The present invention comprises the combination of two orthogonal sensing technologies, namely mass spectrometry and fluorescence and/or absorption spectroscopy, to provide a novel method of oil in water composition determination, detection and monitoring.

Embodiments of the present invention will now be described, by way of example only, with reference to the accompanying drawings, in which:—

FIG. 2 is an example of the data obtained from the mass spectrometer of the apparatus of FIG. 1; and FIG. 3 is an example of data obtained from the fluorescent response measured by the fluorometer as interpreted by the data recorded by the mass spectrometer.

Figure 1:
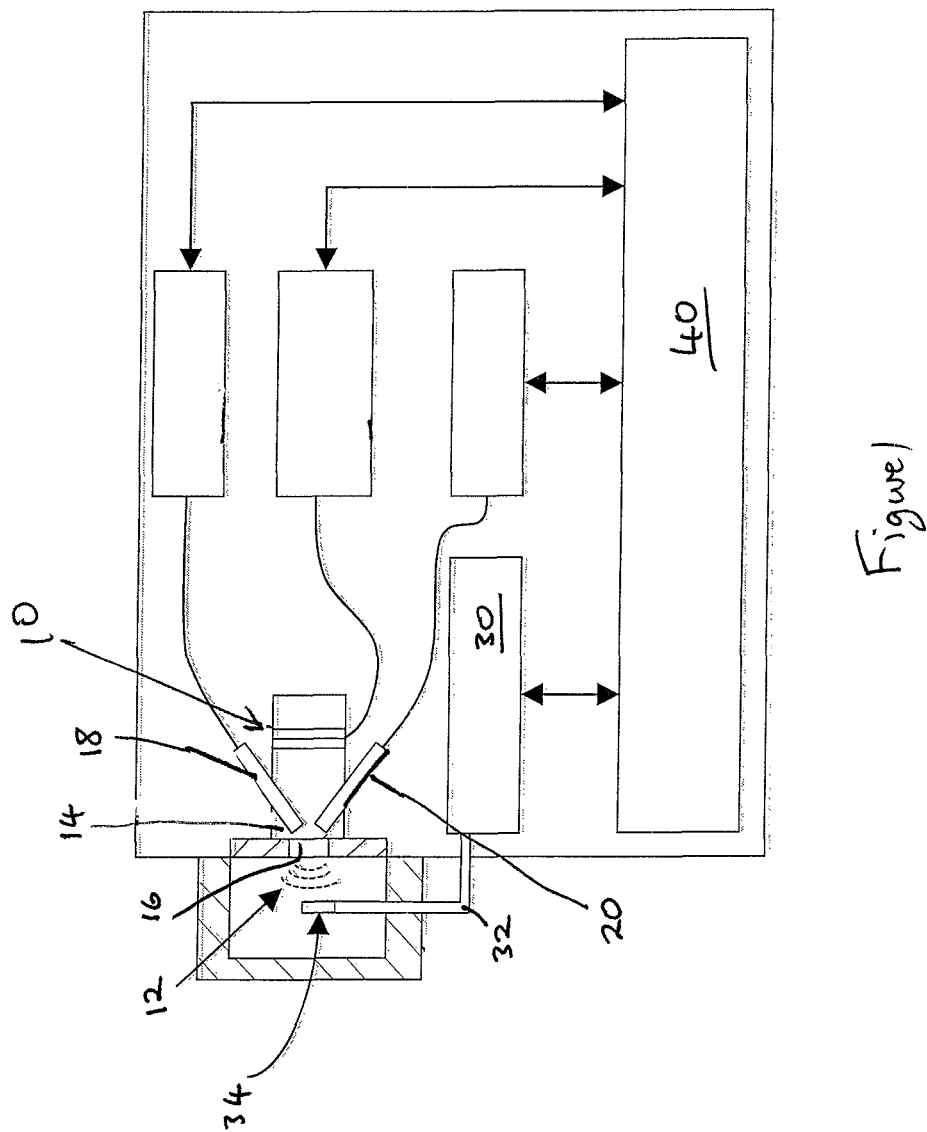
FIG. 1 is a schematic view of an apparatus for determining the amount of two or more substances in accordance with an embodiment of the present invention.

In an embodiment of the present invention as illustrated in FIG. 1, the apparatus includes a fluorometer 10 for measuring fluorescence in a liquid comprising an in-line fluorometer for incorporation, in use, into a pipe or conduit through which a liquid (e.g. water) including two or more other substances (e.g. two or more types of oil) flows. In the following description, the liquid is assumed to comprise water and the other substances are assumed to comprise two or more distinct types of oil, although it will be understood that that the invention is not limited to these.

The apparatus comprises a primary measurement chamber 12, which may be provided by a section of pipe or conduit that is separately formed from the pipe or conduit but is adapted for in-line connection therewith using any suitable conventional connectors (not shown). The fluorometer 10 may be of the type shown in EP 1991856 and therefore need not be described in more detail herein, although the fluorometer is preferably of the type incorporating an ultrasonic transducer 14 for cleaning a measurement window 16 of the fluorometer 10. The fluorometer 10 comprises an excitation source 18 in the form of a 3 mW laser diode module of 405 nm wavelength and a detector 20 for detecting the fluorescent response of a target substance over a range of frequencies/wavelengths to produce a response spectrum for the substance.

The apparatus further comprises a membrane introduction mass spectrometer 30 having an evacuated chamber 32 communicating with an inlet duct terminating in the measurement chamber. A permeable hydrophobic membrane 34 is provided at a distal end of the inlet duct to be located within the measurement chamber. Said membrane may form a portion of a wall of the measurement chamber of the apparatus such that hydrocarbon compounds within a liquid, such as water, contained within, or flowing through, the measurement chamber may pass through the membrane to be ionised within the evacuated chamber of the mass spectrometer such that the relative proportions of each hydrocarbon compound within the liquid may be determined. However, in the embodiment shown in FIG. 1, the membrane 34 is located at a distal end of the inlet duct adjacent the measurement window 16 of the fluorometer 10 so that the membrane is exposed to ultrasonic waves from the ultrasonic transducer 14, such that the ultrasonic waves prevent the membrane from becoming blocked by contaminants. The membrane 34 is preferably formed from a hydrophobic material so that water does not pass through the membrane. A suitable material is polydiemthylsoloxane (PDMS).

In an alternative embodiment, the entrance port of the mass spectrometer may be provided in a further measurement chamber preferably connected to said pipe or conduit to be arranged in parallel to the primary measurement chamber. Valves may be provided for periodically diverting at least a portion of the liquid flowing through the pipe or conduit to flow through the further measurement to enable periodic determination of the presence and relative proportions/concentration of fluorescent substances, and other compounds, present in the liquid flowing through said pipe or conduit to provide data to be used, in combination with the data from the fluorometer, to determine the amount of each of said two or more fluorescent substances present in the liquid.

In membrane introduction mass spectrometers (MIMS) hydrocarbon compounds (and other compounds) present in water are transported to the mass spectrometer by a three stage process termed pervaporation. The compounds are first transferred from the liquid to the surface of the membrane, diffuse through the membrane and are evaporated from the other side, either directly into the mass spectrometer vacuum system or into a stream of inert gas which transports the analyte to the ion source. The membrane may comprise a Silicone (polydimethysiloxane) membrane. However, a variety of other membrane materials may also be suitable. The data from the mass spectrometer identifies each compound present and determines the relative proportions or concentrations of the compounds contained in the liquid.

The apparatus further comprises a processing means, in the form of a microprocessor 40, which receives data from both the mass spectrometer and the fluorometer.

In a first stage, the mass spectrometer is operated to identify each substance present within the liquid and to determine the amount of each substance within the liquid based upon calibration data for each substance identified. This data is recorded in a memory store of the microprocessor 40 as a record of the amount of each substance and the sum total amount of material present in the liquid.

In a second stage the fluorometer is operated to determine a fluorescent response resulting from excitation of the mixture in the measurement chamber 12. The microprocessor 40 interprets the fluorescent response and determines the total amount material present from previous calibration data as a function of the fluorescent response. This result is compared to the amount determined from the first stage and a calibration factor is determined to correct the result to match that determined from the mass spectrometer.

This calibration factor is applied to subsequent measurements of the fluorescent response to determine an accurate measurement of the total amount of material present in the liquid based upon the fluorescent response of the fluorescent substances present in the liquid. The fluorometer 10 can therefore be operated continuously to provide a real time assessment of the amount of each substance present in the liquid in the measurement chamber 12 based upon the detected fluorescent response data as interpreted by the recorded data from the most recent operation of the mass spectrometer 30.

This calibration factor can continue to be used for as long as the relative proportions of substances present in the liquid, in particular fluorescent substances and non-fluorescent substances, do not change. After a predetermined period of time the first stage of the process may be repeated to provide an accurate measurement of the total amount and relative proportions of the substances present in the liquid. This is again compared to the total amount of material present as determined from the fluorescent response and the calibration factor is adjusted if necessary.

As well as determining the sum total amount of fluorescent and non-fluorescent substances present in the liquid from the fluorescent response measured by the fluorometer, the apparatus enables the individual amount of each substance present to be determined from the fluorescent response based upon the total amount of substance determined and the stored data in respect of the relative proportions of each substance present in the liquid, as measured by the mass spectrometer.

The data obtained from the mass spectrometer is used by the processing means of the microprocessor 40 to deconstruct the data obtained from the fluorometer 10 so that the fluorometer can be used to determine the amount of each compound present in the water, including both fluorescent and non-fluorescent substances.

The mass spectrometer 30 is more sensitive to the harsh environment in which the apparatus may be used, particularly in analysing oil in water in an offshore environment, when compared to the fluorometer 10, and thus the intermittent use of the mass spectrometer 10 to periodically provide updated data to be used to deconstruct and interpret the data repeatedly or continuously obtained from the fluorometer 10, prolongs the life of the mass spectrometer 30, and in particular the membrane 34 thereof.

FIG. 2 shows a typical reading from the mass spectrometer 30, wherein the total amount of hydrocarbons present in a liquid is measured at 1000 parts per million, made up of the six different substances.

FIG. 3 shows five subsequent consecutive readings from the fluorometer 10. In the first the fluorescent response is calibrated to record the same total amount of hydrocarbons present as recorded by the mass spectrometer 30. The amount of each individual hydrocarbon is determined from the relative proportions present as measured by the mass spectrometer 30. Subsequent readings of the fluorometer show the total amount of hydrocarbons present falling to 500 ppm in the fifth reading. Again, the amount of each hydrocarbon present can be determined from the relative proportions as determined from the mass spectrometer 30.

After a predetermined period of time the mass spectrometer 30 can be used to take a new reading to effectively recalibrate the fluorometer 10.

It is envisaged that a single mass spectrometer may be used with several fluorometer devices for simultaneously analysing multiple streams, each stream being analysed by a respective fluorometer device and each stream being periodically diverted to and separately analysed by the mass spectrometer to provide data to be used by the processing means to deconstruct and interpret the date obtained from the respective fluorometer.

By using the mass spectrometer to identify the compounds/substances present and the total amount of each and the proportions in which such compounds/substances are present, such data can subsequently be used to deconstruct and interpret the spectral response data obtained by fluorescent spectroscopy. The required information regarding the amount of each compound present in a liquid sample is present in the spectral response data obtained from the fluorometer. However, the data obtained from the mass spectrometer is required to extract such information from such spectral response data. Thus the combination of the data sets from the two orthogonal sensing techniques enables the required information to be extracted from the fluorescent response of the mixture of two or more fluorescent compounds in water.

It is envisaged that such technique of identifying and determining the relative proportions of two or more compounds in a liquid sample may also be applied to deconstruct and interpret spectral response data obtained from absorption spectroscopy techniques.

The apparatus in accordance with the present invention may also enable the amount of non-fluorescent substances, in particular aliphatic hydrocarbons, present in the water to be determined by the use of the data from the mass spectrometer. The data from the mass spectrometer will identify the presence of such non-fluorescent compounds and the relative concentration of such compounds with respect to the concentration of fluorescent compounds, in particular aromatic compounds. Thus the determined amounts of the fluorescent compounds determined by the fluorometer can be used to estimate the amounts of said non-fluorescent compounds based on the relative concentrations of non-fluorescent and fluorescent compounds determined by the mass spectrometer.

The invention is not limited to the embodiment(s) described herein but can be amended or modified without departing from the scope of the present invention.

The invention claimed is:

1. An apparatus for determining the total amount of two or more substances in a liquid, at least one of said substances comprising a fluorescent substance, said apparatus comprising:
   a mass spectrometer device
   a fluorometer device, and
   a processing means
   wherein said mass spectrometer device is adapted to obtain a periodic measurement of the total amount of said two or more substances in the liquid,
   said fluorometer device being adapted to detect the fluorescent response of said at least one fluorescent substance in said liquid to an excitation signal,
   said processing means being programmed to determine a calibration factor by comparing a measurement obtained by the fluorometer device with said periodic measurement of the total amount of said two or more substances present obtained by the mass spectrometer device,
   the processing means subsequently using said calibration factor to determine measurements representative of the total amount of both fluorescent and non-fluorescent substances present in the liquid based upon the fluorescent response detected by the fluorometer device.

2. An apparatus as claimed in claim 1, wherein said apparatus is adapted to obtain further periodic measurements of the total amount of said two or more substances in the liquid by periodic operation of said mass spectrometer device to update said calibration factor at selected intervals.

3. An apparatus as claimed in claim 2, wherein said processing means includes memory means for recording data obtained from the mass spectrometer device to enable said data to be subsequently used to interpret the spectral response date obtained by the fluorometer device.

4. An apparatus as claimed in claim 3, wherein said memory means is also adapted to record data obtained by the fluorometer device over time.

5. An apparatus as claimed in claim 4, wherein the mass spectrometer device comprises a membrane introduction mass spectrometer (MIMS) having a permeable membrane through which said two or more substances present in the liquid, in particular hydrocarbons, can pass to be ionised within the mass spectrometer device.

6. An apparatus as claimed in claim 5, wherein the mass spectrometer device is provided with an evacuated chamber, said membrane being associated with an entrance port of the evacuated chamber whereby said two or more substances may pass through the membrane to be introduced into the mass spectrometer device.

7. An apparatus as claimed in claim 6, wherein the membrane comprises a hydrophobic membrane.

8. An apparatus as claimed in claim 7, wherein the membrane defines a wall portion of a sampling chamber.

9. An apparatus as claimed in claim 7, wherein the membrane is provided at an end of an evacuated tube extending into the sampling chamber.

10. An apparatus as claimed in claim 7, wherein the membrane is located adjacent a measurement window of the fluorometer device formed in a wall of the sampling chamber.

11. An apparatus as claimed in claim 10, comprising an ultrasonic transducer for applying ultrasonic energy to the membrane to keep the membrane clear from dirt and blockages.

12. An apparatus as claimed in claim 11, wherein said ultrasonic transducer is arranged to propagate ultrasonic energy to the membrane via the liquid adjacent the membrane.

13. An apparatus as claimed in claim 12, wherein the ultrasonic transducer is associated with the fluorometer device such that a viewing window of the fluorometer device is kept clean by means of the ultrasonic transducer.

14. A method of determining the amounts of two or more compounds in a liquid, said method using a first technique to determine the total amount of substantially all compounds present in the liquid and using a second technique to determine the amount of at least one of the two or more compounds present in said liquid, the measurement obtained by the second technique being calibrated by the measurement obtained from the first technique, such that the total amount of said two or more compounds present in the liquid can be determined using the data obtained by said second technique over a period of time based upon an assumption that the relative proportions of said two or more compounds present does not change significantly over said period of time.

15. A method as claimed in claim 14, wherein said total amount of said two or more compounds present is determined using said first technique after said period of time to thereby recalibrate said second technique.

16. A method as claimed in claim 15, wherein said first technique comprises mass spectrometry.

17. A method as claimed in claim 16, wherein said second technique comprises fluoroscopy or absorption spectroscopy.

18. A method as claimed in claim 17, wherein the data obtained by said first technique is used to deconstruct the data obtained by the second technique, whereby the data obtained by the second technique is used to determine the amount or concentration of each of said two or more compounds present within said liquid.

19. A method as claimed in claim 18, wherein said first technique is carried out intermittently to periodically recalibrate said second technique.

20. A method as claimed in claim 19, wherein said second technique is carried out continuously.

21. A method as claimed in claim 20, wherein, once the total amount of said two or more compounds present in said liquid has been determined by said first technique, data obtained by said second technique, calibrated by the data obtained from the first technique, is subsequently used to determine the total amount of said two or more compounds present and may also be used to determine the amount of each of each of said two or more compounds present in said liquid based upon the relative proportions of each of said two or more compounds as determined by the first technique.

\* \* \* \* \*